US005736366A

United States Patent [19]

Margraff

[11] Patent Number: 5,736,366
[45] Date of Patent: Apr. 7, 1998

[54] PROCESS FOR OBTAINING 10-DEACETYLBACCATIN III

[75] Inventor: Rodolphe Margraff, Viry Chatillon, France

[73] Assignee: Rhone-Poulenc Rorer S.A., Antony, France

[21] Appl. No.: 481,208

[22] Filed: Jun. 7, 1995

Related U.S. Application Data

[63] Continuation of Ser. No. 122,630, Sep. 17, 1993, abandoned, which is a continuation of Ser. No. 10,084, Jan. 27, 1993, Pat. No. 5,393,896.

[30] Foreign Application Priority Data

Oct. 5, 1992 [FR] France ........................... 92 11745

[51] Int. Cl.$^6$ ........................... C12P 17/02; C07D 305/00
[52] U.S. Cl. ........................... 435/123; 210/600; 549/510
[58] Field of Search ........................... 435/123; 210/600; 549/510

[56] References Cited

U.S. PATENT DOCUMENTS

| 5,019,504 | 5/1991 | Christen et al. | 435/123 |
| 5,279,953 | 1/1994 | Stahlhut | 435/123 |

OTHER PUBLICATIONS

Rizzo et al. *J. Pharm Biomed Anal.* (1990) vol. 8 (2), pp. 159–164.

*Primary Examiner*—Leon B. Lankford, Jr.
*Attorney, Agent, or Firm*—Finnegan, Henderson, Farabow, Garrett & Dunner, L.L.P.

[57] ABSTRACT

Process for obtaining 10-deacetylbaccatin III from various parts of the yew (Taxus sp.) by extracting, with a suitable organic solvent, the aqueous solution obtained after treatment with water of the appropriate part of the yew or by adsorption of the aqueous solution on an appropriate substrate and desorption of 10-deacetylbaccatin III with a suitable solvent and then selective crystallization of 10-deacetylbaccatin III.

30 Claims, No Drawings

PROCESS FOR OBTAINING 10-DEACETYLBACCATIN III

This is a continuation of application Ser. No. 08/122,630 filed Sep. 17, 1993 now abandoned which is a continuation-in-part of Ser. No. 08/010,084, filed Jan. 27, 1993 now U.S. Pat. No. 5,393,896. This application is hereby incorporated by reference.

The present invention relates to a process for obtaining intermediates which are useful for the preparation, by semi-synthetic processes, of taxol, of Taxotere or of their analogues from different parts of plants containing these intermediates.

More particularly, the invention relates to the selective production of 10-deacetylbaccatin III from the bark, trunk, roots or leaves of different yew species.

BACKGROUND OF THE INVENTION

Taxol and Taxotere as well as their analogues of general formula:

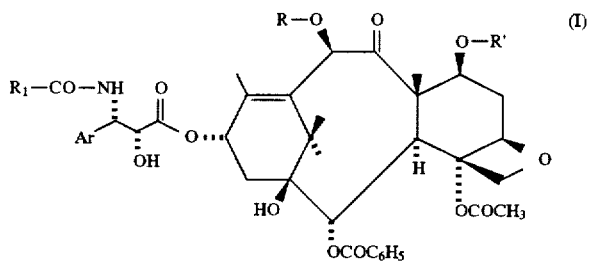

which show notable anticancer and antileukaemia properties, constitute notable chemotherapeutic agents for the treatment of a certain number of cancers, such as, for example, cancers of the breast, prostate, colon, stomach, kidney or testicles and more especially cancer of the ovaries.

Especially, in the general formula (I), Ar can represent an optionally substituted phenyl radical, R can represent a hydrogen atom or an acetyl radical or a N-substituted carbamoyl radical, R' represents a hydrogen atom or a N-substituted carbamoyl radical and $R_1$ can represent a phenyl radical or a radical $R_2$—O— in which $R_2$ represents an alkyl, alkenyl, alkynyl, cycloalkyl, cycloalkenyl, bicycloalkyl, phenyl or heterocyclyl radical.

Taxol corresponds to the product of general formula (I) in which Ar and $R_1$ represent a phenyl radical and R represents an acetyl radical and R' represents a hydrogen atom and Taxotere corresponds to the product of general formula (I) in which Ar represents a phenyl radical, R and R' represent a hydrogen atom and $R_1$ represents a t-butoxy radical.

Taxol, which exists in the natural state in various species of yew in which it is found in small amounts, is difficult to isolate without completely destroying the plant. For example, taxol can be isolated according to the method of C. H. O. Huang et al., J. Natl. Prod., 49, 665 (1986) which consists in treating the ground bark of Taxus brevifolia with methanol, in concentrating the extract, extracting the concentrate with dichloromethane, in concentrating again, in dispersing the residue in a hexane/acetone (1/1 by volume) mixture, and in purifying the soluble part by chromatography on a Florisil column to obtain crude taxol which is purified by successive recrystallizations from methanol/water and hexane/acetone mixtures, then by chromatography and another crystallization. The amounts of taxol thus extracted can represent from 0.005 to 0.017% of the part of the plant used.

Taxotere, which does not exist in the natural state, can be prepared by semi-synthesis from 10-deacetylbaccatin III of formula:

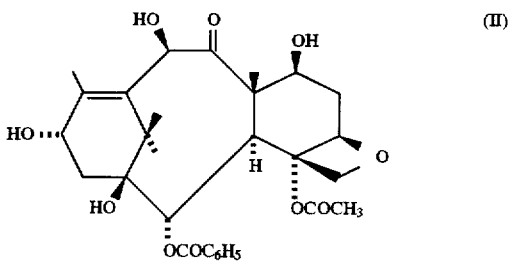

according to the processes which are described, for example, in American Patents U.S. Pat. No. 4,814,470 or U.S. Pat. No. 4,924,012 or in International Application PCT WO 92/09589.

Taxol can also be prepared by processes which involve the use of 10-deacetylbaccatin III, either by passing through the intermediacy of Taxotere under the conditions described in American Patent U.S. Pat. No. 4,857,653 or by esterification of baccatin III under the conditions described in European Patents EP 400,971 or EP 428,376 or by esterification of 10-deactylbaccatin III and acetylation under the conditions described in American Patent U.S. Pat. No. 4,924,011.

The various yew varieties (Taxus baccata, Taxus brevifolia, Taxus canadensis, Taxus cupidata, Taxus floridana, Taxus media or Taxus wallichiana) contain taxane derivatives, the main ones of which are essentially taxol and 10-deacetylbaccatin III, the other derivatives being more particularly cephalomannin, 10-deacetylcephalomannin or baccatin III, optionally linked to sugars.

Whereas taxol is mainly found in the trunk and bark, 10-deacetylbaccatin III is essentially present in the leaves. Moreover, the 10-deacetylbaccatin III content in the leaves is generally much greater than that of taxol, whether the latter is present in the bark, trunk or in the leaves.

It results therefrom that it is particularly important to be able to have available 10-deacetylbaccatin III which is essential to the preparation of much more significant amounts of taxol than by direct extraction from yews as well as to the preparation of Taxotere.

Extracting 10-deacetylbaccatin III from yew leaves does not lead to complete destruction of the plant, whose leaves can be used again after each growth cycle.

Generally, the known methods for extracting taxane derivatives contained in the various parts of the yew (bark, trunk, roots, leaves and the like) require the use of lengthy and expensive chromatographic techniques which do not make possible complete and quantitative separation of the taxane derivatives initially present in the plant.

10-Deacetylbaccatin III can be obtained, with yields in the region of 300 mg per kg of leaves (Taxus baccata), by a process which uses maceration of the needles in ethanol, extraction with an organic solvent, such as methylene chloride, and successively chromatographing according to the process which is described in American Patent U.S. Pat. No. 4,814,470.

The various taxane-derived constituents present in the various parts of the yew can also be separated by methods using "reverse" liquid phase chromatography which are described, in particular, in International Application PCT WO 92/07842. These processes consist essentially in treating the crude yew extracts by "reverse" liquid phase chromatography through an adsorbent on which the taxane derivatives are fixed, in eluting the taxane derivatives and in isolating them. According to this process, it is possible to isolate 200 mg of 10-deacetylbaccatin III from 1 kg of ground and dried leaves.

DESCRIPTION OF THE INVENTION

It has now been found, and it is which forms the subject of the present invention, that 10-deacetylbaccatin III can be extracted very selectively, and with an excellent yield, from the various parts of the yew, and more particularly from the leaves, by a simple process which does not use chromatographic techniques. For example, it is possible to extract approximately 800 mg of 10-deacetylbaccatin III per kg of yew (*Taxus baccata*) leaves.

The process according to the invention consists in isolating 10-deacetylbaccatin III from an aqueous extract of yew leaves.

More particularly, the process according to the invention consists,
either 1) in treating the ground parts of the yew (Taxus sp.) with water, 2) in separating the aqueous solution, containing 10-deacetylbaccatin III, from the suspended plant mass, 3) in extracting 10-deacetylbaccatin III from the aqueous solution with an organic solvent, 4) in separating the organic extract, containing 10-deacetylbaccatin III, from the aqueous phase, 5) in removing the organic solvent from the organic extract thus separated, 6) in selectively crystallizing, in an organic solvent, 10-deacetylbaccatin III from the residue thus obtained, 7) in isolating 10-deacetylbaccatin III in the purified form
or else 1) in treating the ground parts of the yew (Taxus sp.) with water, 2) in separating the aqueous solution, containing 10-deacetylbaccatin III, from the suspended plant mass, 3) in adsorbing the aqueous solution containing 10-deacetylbaccatin III on a suitable substrate 4) in desorbing 10-deacetylbaccatin III using an organic solvent 5) in removing the organic solvent from the desorbate 6) in selectively crystallizing, in an organic solvent, 10-deacetylbaccatin III from the residue thus obtained 7) in isolating 10-deacetylbaccatin III in the purified form.

The process according to the invention can be used on any suitable part of the yew, such as the bark, trunk, roots or leaves. The yew used for the implementation of the process according to the invention preferably belongs to the variety *Taxus baccata, Taxus brevifolia, Taxus canadensis, Taxus cupidata, Taxus floridana, Taxus media* or *Taxus wallichiana*. It is particularly advantageous to use yew leaves (*Taxus baccata, Taxus brevifolia*) which are generally richer in 10-deacetylbaccatin III. The fragments used can have sizes varying from 0.5 to several millimeters. For reasons of convenience, it may be advantageous to use fragments whose mean sizes are less than 1 mm. The ground, and, optionally dried, parts of the yew can be obtained by grinding, and optionally drying, operations which, optionally, precede or follow freezing and defrosting operations of the fresh parts of the plant or are inserted into freezing and defrosting operations of the fresh parts of the plant.

The treatment by water of the ground parts of the yew is carried out according to techniques known to one skilled in the art. In particular, the aqueous solution containing 10-deacetylbaccatin III is generally obtained by stirring, at a temperature between 20° and 65° C., ground parts of the yew in water for 30 minutes to 2 hours. The amount of water used can vary within wide limits; however, it is appropriate to use an amount of water from 2 to 10 liters calculated per kg of ground and dried plant part and preferably approximately 5 liters of water per kg of plant part to be treated. It may be advantageous to use demineralized water to carry out this treatment and to carry out the treatment under ultrasound.

For the purpose of improving the yield, it may be advantageous to carry out several treatments of the plant mass with water in order to obtain aqueous solutions from which 10-deacetylbaccatin III is extracted under the conditions described below.

The aqueous solution obtained containing 10-deacetylbaccatin III is separated from the plant mass by the usual techniques such as filtration, centrifuging or settling. The resulting aqueous solution, optionally cooled, can be treated according to one of the following ways:

1) 10-deacetylbaccatin III is extracted, one or a number of times, with an organic solvent. Organic solvents which are particularly well suited are chosen from ethers such as methyl t-butyl ether, ethyl t-butyl ether, methyl n-butyl ether, methyl n-amyl ether, ethyl t-amyl ether, t-butyl isopropyl ether, ethyl isobutyl ether, t-butyl n-propyl ether or ethyl n-hexyl ether and aliphatic esters such as ethyl acetate, propyl acetate, isopropyl acetate, n-butyl acetate, t-butyl acetate, methyl t-butylacetate, t-butyl propionate or t-amyl acetate. Methyl t-butyl ether, ethyl t-butyl ether, ethyl acetate or n-butyl acetate are very particularly advantageous.

Extraction with an organic solvent is generally carried out on an aqueous solution whose pH is less than 7 and preferably less than 6.

The organic extracts, containing 10-deacetylbaccatin III, are separated from the aqueous phase by application of the usual techniques such as settling.

The organic extracts are optionally washed using an aqueous solution of a weak base (aqueous sodium carbonate solution, for example) and/or with water. After drying, the organic solvent of the extract is removed according to the usual methods and in particular by distillation, optionally under reduced pressure, to give a, generally solid, residue from which 10-deacetylbaccatin III is isolated.

2) the aqueous solution is adsorbed on a suitable substrate in order to fix 10-deacetylbaccatin III. There is used, as substrate, an adsorbing resin which is preferably chosen from polystyrene/divinylbenzene resins.

Desorption of 10-deacetylbaccatin III is carried out by washing the substrate with a suitable solvent. There is preferably used, as solvent, an aliphatic alcohol containing 1 to 3 carbon atoms and more particularly methanol.

The organic solution is separated from the substrate, generally by filtration, and is then concentrated to dryness, generally by distillation, optionally under reduced pressure, to give a, generally solid, residue from which 10-deacetylbaccatin III is isolated.

Selective crystallization of crude 10-deacetylbaccatin III, obtained according to one or the other route, is carried out from a solution of the residue obtained in an organic solvent or in a mixture of organic solvents. There may be advantageously used, as solvents which make it possible to selectively crystallize 10-deacetylbaccatin III, nitriles such as acetonitrile, propionitrile or isobutyronitrile, optionally mixed with an aliphatic alcohol such as methanol, ethanol, propanol, isopropanol or n-butanol or an aliphatic ester such as ethyl acetate, isopropyl acetate, n-butyl acetate or t-butyl acetate or an aliphatic ketone such as acetone, methyl ethyl ketone, methyl propyl ketone, methyl n-butyl ketone or methyl isobutyl ketone. It is particularly advantageous to carry out the selective crystallization from acetonitrile, optionally in the presence of ethanol and/or of ethyl or n-butyl acetate and/or of acetone.

10-Deacetylbaccatin III, which precipitates, can be separated by filtration, settling or centrifuging.

The process according to the invention makes it possible to obtain virtually pure 10-deacetylbaccatin III with yields generally much greater than those obtained by using the previously known processes. The process according to the invention makes it possible to virtually quantitatively extract all the 10-deacetylbaccatin III contained in the parts of the plant used and in particular leaves.

10-Deacetylbaccatin III obtained according to the extraction process of the present invention can be used to prepare taxol or Taxotere or their derivatives under the conditions which are described more particularly in Patents EP 0,253, 738, EP 0,253,739, EP 0,336,841, EP 0,336,840, WO 92 09589, EP 0,400,971 and EP 0,428,376.

EXAMPLES

The following examples illustrate the process according to the invention.

Example 1

500 g of ground and dried yew leaves (*Taxus baccata*), in which the mean size of the particles is less than 1 mm and in which the 10-deacetylbaccatin III assay, determined by high performance liquid chromatography (HPLC), is 0.08% (i.e. 400 mg of 10-deacetylbaccatin III in 500 g of leaves), are added to 2.5 liters of demineralized water heated to 50° C. The mixture is stirred for 1 hour at 50° C. and then filtered.

The filtrate (1.8 liters), the pH of which is 5.4, is extracted with 3 times 0.9 liter of ethyl acetate. The combined organic phases (2.7 liters) are washed twice with 1 liter of a 0.1M sodium carbonate solution, then with 2 times 1 liter of demineralized water and finally dried over sodium sulphate. After filtration and concentration to dryness, a solid (3.2 g) is obtained which is taken up in 9 cm$^3$ of acetonitrile at a temperature in the region of 70° C. After cooling overnight at a temperature in the region of +4° C., the precipitate is separated by filtration. There are thus obtained, after drying, 245 mg of crystals containing, after analysis by HPLC, 75% of pure 10-deacetylbaccatin III, i.e. 183 mg. The mother liquors, according to analysis by HPLC, contain 40 mg of 10-deacetylbaccatin III.

The plant mass, which has retained 0.7 liter of water, is extracted twice under the conditions described above. The combined aqueous filtrates are treated as above. There are thus obtained 2.5 g of a solid product which is taken up in 5 cm$^3$ of acetonitrile at a temperature in the region of 70° C. After cooling overnight at a temperature in the region of +4° C., 169 mg of crystals are separated by filtration, these crystals containing, according to analysis by HPLC, 75% of pure 10-deacetylbaccatin III, i.e. 127 mg. The mother liquors contain, according to analysis by HPLC, 47 mg of 10-deacetylbaccatin III.

The total amount of 10-deacetylbaccatin III extracted by the water is 183+40+127+47=397 mg.

The yield is virtually quantitative.

Example 2

3 liters of demineralized water are heated to 50° C. and then 500 g of ground and dried yew leaves, the mean diameter of the particles of which is 1 mm and the 10-deacetylbaccatin III assay of which, determined by high performance liquid chromatography (HPLC), is 0.08% (i.e. 400 mg of 10-deacetylbaccatin III in 500 g of leaves), are added. The mixture is stirred for 1 hour at 50° C. and then filtered. The filtrate (1.97 liter), the pH of which is 5.15, is adjusted to pH=4.6 by addition of concentrated hydrochloric acid and is then filtered through a membrane made of asbestos board in a Seitz filter. 1.8 liters of filtrate are collected.

300 cm$^3$ of filtrate are extracted with 2 times 150 cm$^3$ and then 4 times 60 cm$^3$ of methyl tert-butyl ether (MTBE). The combined and concentrated extracts provide 620 mg of solids which are taken up in 3 cm$^3$ of acetonitrile at 70° C.

After cooling overnight at +4° C., 28 mg of crystallized 10-deacetylbaccatin III are separated by filtration, the assay of which, determined by HPLC, is 90%. The mother liquors contain 12.8 mg of 10-deacetylbaccatin III (assaying by HPLC).

Example 3

1 kg of freshly cut yew (*Taxus baccata*) leaves, the water content of which is 69% and the 10-deacetylbaccatin III content of which is 651 mg/kg (determination by HPLC), is ground in a 2-liter mixer in the presence of demineralized water in 10 successive identical operations using, each time, 100 g of leaves and 500 cm$^3$ of water at a temperature in the region of 20° C. The mixture obtained is filtered through a cotton cloth and then through paper, rinsing with a total of 200 cm$^3$ of water. 5,000 cm$^3$ of filtrate are collected, i.e. 84.9% of the total volume of water (water used and water contained in the leaves). According to the quantitative determination by HPLC, the aqueous solution thus obtained contains 72 g of solids, including 550 mg of 10-deacetylbaccatin III, i.e. virtually the theoretical amount of 552.7 mg (84.9% of 651 mg). The remainder of the 10-deacetylbaccatin III, contained in the water impregnating the plant material, can be recovered by washing the plant material with water.

The aqueous solution (5,000 cm$^3$) is percolated through a column with a diameter of 5 cm filled over a height of 10 cm with a polystyrene/divinylbenzene resin (Amberchrom CG 161 md® (Tosohaas, Stuttgart, Germany).

The resin is rinsed with water, dried and then suspended in methanol.

After filtration and concentration to dryness of the filtrate, a residue (15.5 g) is obtained which is taken up in 100 cm$^3$ of ethyl acetate. 8.7 g of an insoluble product are separated by filtration and the filtrate is then concentrated to a volume of 5 cm$^3$. 30 cm$^3$ of acetonitrile are added. A clear solution is obtained in which white crystals very rapidly appear. After standing overnight at 4° C. the white crystals are separated by filtration and dried. There are thus obtained 548 mg of 10-deacetylbaccatin III, solvated with one mole of acetonitrile, with a yield of 92%.

Quantitative determination by HPLC with internal standardization shows that these crystals contain 82% of 10-deacetylbaccatin III.

The 10-deacetylbaccatin III yield is thus 75.4%.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

I claim:

1. A process for obtaining 10-deacetylbaccatin III from an aqueous extract of the bark, trunk, roots or foliage of the yew (Taxus sp.), said process comprising the following steps:

1) grinding at least one plant part selected from the bark, trunk, roots or foliage of the yew (Taxus sp) and optionally drying the at least one ground part, 2) treating the at least one ground part of the yew (Taxus sp.) with water to form an aqueous suspension, 3) separating the aqueous solution, containing 10-deacetylbaccatin III, from the suspended plant mass, 4) adsorbing the aqueous solution containing 10-deacetylbaccatin III on a suitable substrate, 5 desorbing 10-deacetylbaccatin III, using an organic solvent, 6) removing the organic solvent from the desorbate, 7) selectively crystallizing 10-deacetylbaccatin III in an organic solvent, from the residue thus obtained, and 8 isolating 10-deacetylbaccatin III in the purified form.

2. A process according to claim 1, wherein the at least one ground, and optionally dried, part of the yew is treated with water by stirring said at least one part of the yew with water at a temperature ranging from 20° to 65° C.

3. A process according to claim 2, wherein said grinding and drying operations optionally precede or follow freezing and defrosting operations of the at least one plant part or are carried out during freezing and defrosting operations of the at least one plant part.

4. A process according to claim 3, wherein demineralized water is used.

5. A process according to claim 3, wherein said treatment by water of said at least one part of the yew is carried out under ultrasound.

6. A process according to claim 2, wherein from 2 to 10 liters of water per kg of said at least one ground plant part is used to treat said at least one plant part.

7. A process according to claim 6, wherein demineralized water is used.

8. A process according to claim 6, wherein said treatment by water of said at least one part of the yew is carried out under ultrasound.

9. A process according to claim 2, wherein demineralized water is used.

10. A process according to claim 2, wherein said treatment by water of said at least one part of the yew is carried out under ultrasound.

11. A process according to claim 1, wherein the aqueous solution containing 10-deacetylbaccatin III is separated from the suspended plant mass by filtration, centrifuging or by settling.

12. A process according to claim 1, wherein the aqueous solution is adsorbed per percolating through a resin.

13. A process according to claim 12, wherein the resin is a polystyrene/divinylbenzene resin.

14. A process according to claim 1, wherein desorption of 10-deacetylbaccatin III from the resin is carried out using an organic solvent.

15. A process according to claim 14, wherein the organic solvent is selected from aliphatic alcohols containing 1 to 3 carbon atoms.

16. A process according to claim 15, wherein the organic solvent is methanol.

17. A process according to claim 1, wherein the organic solution containing 10-deacetylbaccatin III is concentrated to dryness.

18. A process according to claim 17, wherein concentrating is carried out by distillation, optionally under reduced pressure.

19. A process according to claim 1, wherein 10-deacetylbaccatin III is selectively crystallized, in an organic solvent or in a mixture of organic solvents, from the residue obtained after removal of the solvent.

20. A process according to claim 19, wherein the solvent is selected from aliphatic nitriles, optionally mixed with an aliphatic alcohol or an aliphatic ester or an aliphatic ketone.

21. A process according to claim 20, wherein the nitriles are from acetonitrile and propionitrile.

22. A process according to claim 20, wherein the aliphatic alcohol is selected from methanol, ethanol, propanol, isopropanol and n-butanol.

23. A process according to claim 20, wherein the aliphatic ester is selected from ethyl acetate, isopropyl acetate, n-butyl acetate and t-butyl acetate.

24. A process according to claim 20, wherein the aliphatic ketone is selected from acetone, methyl ethyl ketone, methyl propyl ketone, methyl n-butyl ketone and methyl isobutyl ketone.

25. A process according to claim 20, wherein selective crystallization is carried out from acetonitrile, optionally in combination with ethanol and/or ethyl or n-butyl acetate and/or acetone.

26. A process according to claim 1, wherein 10-deacetylbaccatin III is isolated by filtration, settling, or centrifuging.

27. A process according to claim 1, wherein said 10-deacetylbaccatin III is extracted from the foliage of the yew.

28. A process according to claim 1, wherein said yew is of a variety selected from *Taxus baccata, Taxus brevifolia, Taxus canadensis, Taxis cupidata, Taxus floridana, Taxus media* and *Taxus wallichiana*.

29. A process for obtaining 10-deacetylbaccatin III from an aqueous extract of the bark, trunk, roots or foliage of the yew (Taxus sp.), said process comprising the following steps:

(i) treating at least ore plant part selected from the bark, trunk, roots, or foliage of the yew (Taxus sp.) with water, and (ii) removing with an organic solvent said 10-deacetylbaccatin III from said water-treated at least one plant part.

30. A process comprising the step of obtaining 10-deacetylbaccatin III from an aqueous extract of at least one plant part selected from the bark, trunk, roots, or foliage of the yew (Taxus sp.).

* * * * *

UNITED STATES PATENT AND TRADEMARK OFFICE
CERTIFICATE OF CORRECTION

PATENT NO. : 5,736,366
DATED : April 07, 1998
INVENTOR(S) : Rodolphe MARGRAFF

It is certified that error appears in the above-identified patent and that said Letters Patent is hereby corrected as shown below:

Claim 1, column 7, line 2, "sp" should read --sp.--.

Claim 1, column 7, line 11, "5desorbing" should read --5) desorbing--; and "10-deacetyibaccatin" should read --10-deacetylbaccatin--.

Claim 1, column 7, line 17, "8isolating" should read --8) isolating--.

Claim 11, column 7, line 46, "I11" should read --III--.

Claim 29, column 8, line 47, "ore" should read --one--.

UNITED STATES PATENT AND TRADEMARK OFFICE
CERTIFICATE OF CORRECTION

PATENT NO. : 5,736,366
DATED : April 07, 1998
INVENTOR(S) : Rodolphe MARGRAFF

It is certified that error appears in the above-identified patent and that said Letters Patent is hereby corrected as shown below:

Claim 30, column 8, line 54, "10-deacetyibaccatin Ill" should read --10-deacetylbaccatin III--.

Signed and Sealed this

Ninth Day of March, 1999

*Attest:*

Q. TODD DICKINSON

*Attesting Officer*     *Acting Commissioner of Patents and Trademarks*